United States Patent
Semenov

(10) Patent No.: US 11,892,491 B2
(45) Date of Patent: Feb. 6, 2024

(54) ELECTROMAGNETIC INTERFERENCE PATTERN RECOGNITION TOMOGRAPHY

(71) Applicant: EMTensor GmbH, Vienna (AT)

(72) Inventor: Serguei Y. Semenov, Vienna (AT)

(73) Assignee: EMTensor GmbH, Vienna (AT)

( * ) Notice: Subject to any disclaimer, the term of this patent is extended or adjusted under 35 U.S.C. 154(b) by 150 days.

(21) Appl. No.: 17/174,003

(22) Filed: Feb. 11, 2021

(65) Prior Publication Data

US 2021/0181246 A1 Jun. 17, 2021

Related U.S. Application Data

(63) Continuation of application No. 15/953,694, filed on Apr. 16, 2018, now Pat. No. 10,921,361, which is a
(Continued)

(51) Int. Cl.
*A61B 5/055* (2006.01)
*G01R 29/08* (2006.01)
(Continued)

(52) U.S. Cl.
CPC ........ *G01R 29/0892* (2013.01); *A61B 5/0042* (2013.01); *A61B 5/0536* (2013.01);
(Continued)

(58) Field of Classification Search
CPC ... G01R 29/0892; A61B 34/20; A61B 5/0042; A61B 5/0536; A61B 2034/2051; A61B 5/0507
See application file for complete search history.

(56) References Cited

U.S. PATENT DOCUMENTS

| 4,135,131 A | 1/1979 | Larsen et al. |
| 4,157,472 A | 6/1979 | Beck, Jr. et al. |

(Continued)

FOREIGN PATENT DOCUMENTS

| CA | 2936145 | 6/2021 |
| CN | 102132149 | 7/2011 |

(Continued)

OTHER PUBLICATIONS

Semenov, Bulyshev, Souvorov, Svenson, Sizov, Borisov, Posukh, Kozlov, Nazarov, and Tatsis, "Microwave Tomography: Theoretical and Experimental Investigation of the Iteration Reconstruction" Feb. 1998, IEEE Transactions on Microwave Theory and Techniques, vol. 46, No. 2, pp. 135-141. (Year: 1998).*

(Continued)

*Primary Examiner* — John E Breene
*Assistant Examiner* — Christine Y Liao
(74) *Attorney, Agent, or Firm* — Tillman, Wright & Wolgin; James D. Wright; David R. Higgins

(57) ABSTRACT

An Electromagnetic Interference Pattern Recognition Tomography (EMIPRT) method for use in an image reconstruction system includes generating electromagnetic field data corresponding to an object in an imaging domain, via an electromagnetic tomography system, and using the generated electromagnetic field data, repeatedly, in recursive manner, forming an undisturbed electromagnetic interference image, forming a disturbed electromagnetic interference image based on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image. Forming a disturbed electromagnetic (Continued)

interference image is also based on an object factor that is a function of the differences between experimentally electromagnetic fields and electromagnetic fields calculated during the step of forming an undisturbed electromagnetic interference image. After each repeated step of forming a superposition image, the method also includes determining whether a convergence objective has been reached.

22 Claims, 8 Drawing Sheets

Related U.S. Application Data continuation of application No. PCT/US2016/057254, filed on Oct. 16, 2016.

(60) Provisional application No. 62/242,915, filed on Oct. 16, 2015.

(51) Int. Cl.
 *A61B 5/00* (2006.01)
 *A61B 5/0536* (2021.01)
 *A61B 34/20* (2016.01)
 *A61B 5/0507* (2021.01)

(52) U.S. Cl.
 CPC ............ *A61B 34/20* (2016.02); *A61B 5/0507* (2013.01); *A61B 2034/2051* (2016.02)

(56) References Cited

U.S. PATENT DOCUMENTS

| | | | |
|---|---|---|---|
| 4,247,815 A | 1/1981 | Larsen et al. | |
| 4,257,278 A | 3/1981 | Papadofrangakis et al. | |
| 4,638,813 A | 1/1987 | Turner | |
| 4,662,222 A | 5/1987 | Johnson | |
| 4,798,209 A | 1/1989 | Klingenbeck et al. | |
| 4,805,627 A | 2/1989 | Klingenbeck et al. | |
| 4,926,868 A | 5/1990 | Larsen | |
| 5,069,223 A | 12/1991 | McRae | |
| 5,222,501 A | 6/1993 | Ideker et al. | |
| 5,233,713 A | 8/1993 | Murphy et al. | |
| 5,263,050 A | 11/1993 | Sutterlin et al. | |
| 5,305,748 A | 4/1994 | Wilk | |
| 5,363,050 A | 11/1994 | Guo et al. | |
| 5,405,346 A | 4/1995 | Grundy et al. | |
| 5,715,819 A | 2/1998 | Svenson et al. | |
| 5,800,350 A | 9/1998 | Coppleson et al. | |
| 6,026,173 A | 2/2000 | Svenson et al. | |
| 6,073,047 A | 6/2000 | Barsamian et al. | |
| 6,332,087 B1 | 12/2001 | Svenson et al. | |
| 6,333,087 B1 | 12/2001 | Jerdee et al. | |
| 6,490,471 B2 | 12/2002 | Svenson et al. | |
| 6,503,203 B1 | 1/2003 | Rafter et al. | |
| 6,511,427 B1 | 1/2003 | Sliwa, Jr. et al. | |
| 6,522,910 B1 | 2/2003 | Gregory | |
| 6,697,660 B1 | 2/2004 | Robinson | |
| 6,865,494 B2 | 3/2005 | Duensing et al. | |
| 7,239,731 B1 | 7/2007 | Semenov et al. | |
| 7,272,431 B2 | 9/2007 | McGrath | |
| 7,340,292 B2 | 3/2008 | Li | |
| 7,876,114 B2 | 1/2011 | Campbell et al. | |
| 8,000,775 B2 | 8/2011 | Pogue et al. | |
| 8,089,417 B2 | 1/2012 | Popovic et al. | |
| 8,207,733 B2 | 6/2012 | Meaney et al. | |
| 8,253,619 B2 | 8/2012 | Holbrook et al. | |
| 8,376,948 B2 | 2/2013 | Brannan | |
| 8,708,919 B1 | 4/2014 | Frazier | |
| 8,724,864 B2 | 5/2014 | Persson et al. | |
| 9,072,449 B2 | 7/2015 | Semenov | |
| 9,414,749 B2 | 8/2016 | Semenov | |
| 9,414,763 B2 | 8/2016 | Semenov | |
| 9,414,764 B2 | 8/2016 | Semenov | |
| 9,675,254 B2 | 6/2017 | Semenov | |
| 9,675,255 B2 | 6/2017 | Semenov | |
| 9,724,010 B2 | 8/2017 | Semenov | |
| 9,924,873 B2 | 3/2018 | Semenov | |
| 10,492,700 B2 | 12/2019 | Semenov | |
| 10,921,361 B2 | 2/2021 | Semenov | |
| 10,980,421 B2 | 4/2021 | Semenov | |
| 10,980,435 B2 | 4/2021 | Semenov | |
| 2002/0017905 A1 | 2/2002 | Conti | |
| 2002/0168317 A1 | 11/2002 | Daighighian et al. | |
| 2002/0191744 A1 | 12/2002 | Mirabelle | |
| 2003/0018244 A1 | 1/2003 | Haddad et al. | |
| 2003/0088180 A1 | 5/2003 | Van Veen et al. | |
| 2003/0090276 A1 | 5/2003 | Weide et al. | |
| 2004/0015087 A1 | 1/2004 | Boric-Lubecke et al. | |
| 2004/0123667 A1 | 7/2004 | McGrath | |
| 2004/0174948 A1 | 9/2004 | Kojima et al. | |
| 2004/0220465 A1 | 11/2004 | Cafarella | |
| 2005/0119569 A1 | 6/2005 | Ohtake | |
| 2005/0135560 A1 | 6/2005 | Dafni et al. | |
| 2005/0203387 A1 | 9/2005 | Godshalk et al. | |
| 2006/0133564 A1 | 6/2006 | Langan et al. | |
| 2006/0247531 A1 | 11/2006 | Pogue et al. | |
| 2006/0276714 A1 | 12/2006 | Holt et al. | |
| 2007/0025514 A1 | 2/2007 | Lawaczeck | |
| 2007/0238957 A1 | 10/2007 | Yared | |
| 2008/0319437 A1 | 12/2008 | Turner et al. | |
| 2009/0015832 A1 | 1/2009 | Popovic et al. | |
| 2009/0292195 A1 | 11/2009 | Boyden et al. | |
| 2010/0010340 A1 | 1/2010 | Godavarty et al. | |
| 2010/0067770 A1 | 3/2010 | Persson et al. | |
| 2010/0174179 A1 | 7/2010 | Persson et al. | |
| 2011/0022325 A1 | 1/2011 | Craddock et al. | |
| 2011/0263961 A1 | 10/2011 | Craddock et al. | |
| 2011/0295102 A1 | 12/2011 | Lakkis et al. | |
| 2012/0010493 A1 | 1/2012 | Semenov | |
| 2012/0083683 A1 | 4/2012 | Kuwabara | |
| 2012/0083690 A1 | 4/2012 | Semenov | |
| 2012/0172954 A1 | 7/2012 | Zastrow et al. | |
| 2012/0179037 A1 | 7/2012 | Halmann | |
| 2012/0190977 A1 | 7/2012 | Persson et al. | |
| 2013/0002264 A1 | 1/2013 | Gaerber | |
| 2013/0190599 A1 | 7/2013 | Wyeth et al. | |
| 2013/0257426 A1 | 10/2013 | Feiweier et al. | |
| 2014/0024917 A1 | 1/2014 | McMahon et al. | |
| 2014/0155740 A1* | 6/2014 | Semenov | A61B 5/0042 600/425 |
| 2014/0275944 A1 | 9/2014 | Semenov | |
| 2014/0276012 A1 | 9/2014 | Semenov | |
| 2014/0378812 A1 | 12/2014 | Saroka et al. | |
| 2015/0117596 A1* | 4/2015 | Cao | A61B 6/5264 378/20 |
| 2015/0257648 A1 | 9/2015 | Semenov | |
| 2015/0257649 A1 | 9/2015 | Semenov | |
| 2015/0342472 A1 | 12/2015 | Semenov | |
| 2016/0256109 A1 | 9/2016 | Semenov | |
| 2016/0262623 A1 | 9/2016 | Semenov | |
| 2016/0324489 A1 | 11/2016 | Crawford et al. | |
| 2016/0345856 A1 | 12/2016 | Semenov | |
| 2017/0127946 A1 | 5/2017 | Levinson et al. | |
| 2017/0273563 A1 | 9/2017 | Semenov | |
| 2018/0231594 A1 | 8/2018 | Semenov | |
| 2018/0235486 A1 | 8/2018 | Semenov | |
| 2018/0344165 A1 | 12/2018 | Semenov | |
| 2019/0313937 A1 | 10/2019 | Fhager et al. | |
| 2021/0082160 A1 | 3/2021 | Abbosh et al. | |
| 2021/0228085 A1 | 7/2021 | Semenov | |
| 2021/0236008 A1 | 8/2021 | Semenov | |

FOREIGN PATENT DOCUMENTS

| | | |
|---|---|---|
| CN | 108366771 A | 8/2018 |
| EP | 3361955 A1 | 8/2018 |
| EP | 3361955 B1 | 9/2020 |
| EP | 2922464 | 9/2021 |
| IL | 241600 | 4/2021 |
| IL | 258655 | 9/2021 |
| RU | 2449729 C2 | 5/2012 |
| WO | 9532665 | 12/1995 |

(56) References Cited

FOREIGN PATENT DOCUMENTS

| WO | 199852464 A1 | 11/1998 |
|---|---|---|
| WO | 200015109 A1 | 3/2000 |
| WO | 00/64343 A1 | 11/2000 |
| WO | 2005115235 A1 | 12/2005 |
| WO | 2007136334 A1 | 11/2007 |
| WO | 2008002251 A1 | 1/2008 |
| WO | 2010100649 A1 | 9/2010 |
| WO | 2011009945 A2 | 1/2011 |
| WO | 2011156810 A2 | 12/2011 |
| WO | 2011156810 A3 | 12/2011 |
| WO | 2013005134 A2 | 1/2013 |
| WO | 2013005134 A3 | 1/2013 |
| WO | 2016036946 A1 | 3/2016 |
| WO | 2017066731 A1 | 4/2017 |
| WO | 2017066731 A8 | 5/2018 |
| WO | 2018127434 A1 | 7/2018 |
| WO | 2019094877 A1 | 5/2019 |
| WO | 2019224266 A1 | 11/2019 |

OTHER PUBLICATIONS

Information Disclosure Statement (IDS) Letter Regarding Common Patent Application(s), dated Feb. 24, 2021.

Mariappan et.al., Magnetoacoustic tomography with magnetic induction for high-resolution bioimepedance imaging through vector source reconstruction under the static field of MRI magnet., Med Phys. Feb. 2014; 41(2): 022902.

Abubakar, A.; van den Berg, P.M. and Mallorqui, J.J. (2002). "Imaging of biomedical data using a multiplicative regularized contrast source inversion method", IEEE Transactions of Microwave Theory and Techniques 50 : 1761-1771. (10 pages).

Bulyshev, A.E.; Souvorov, A.E.; Semenov, S. Y. ; Posukh, V.G. and Sizov, Y. E. (2004). "Three-dimensional vector microwave tomography: theory and computational experiments", Inverse Problems 20 : 1239.

Bulyshev, A.E.; Souvorov, A. E.; Semenov, S.Y.; Svenson, R.H.; Nazarov, A.G.; Sizov, Y.E. and Tatsis, G. P. (2000) "Three-dimensional microwave tomography. Theory and computer experiments in scalar approximation", Inverse Problems 16 : 863.

Chew, W. C. and Wang, Y. M. (1990). "Reconstruction of two-dimensional permittivity distribution using the distorted Born iterative method", IEEE Transactions on Medical Imaging 9 : 218-225. (8 pages).

Devaney, A. J. (1992). Current research topics in diffraction tomography. In: Bertero, M. & Pike, E. (Ed.), Inverse Problems in Scattering and Imaging, Adam Hilger, New York.

Fear, Elise C., et al. "Confocal microwave imaging for breast cancer detection: Localization of tumors in three dimensions." IEEE Transactions of Biomedical Engineering 49.8 (2002): 812-822. (11 pages).

Harada, H.; Wall, D. J. N.; Takenaka, T. and Tanaka, M. (1995). "Conjugate gradient method applied to inverse scattering problem", IEEE Transactions on Antennas and Propagation 43 : 784-792. (9 pages).

Hawley, M.S., et al., "Microwave Imaging of Tissue Blood Content Changes," Journal of Biomedical Engineering (1991), pp. 197-202, vol. 13, No. 3, published by Butterworth-Heinermann for BES (6 pages).

Igney et al. "Design and performance of a planar-array MIT system with normal sensor alignment: Planar-array MIT system with normal sensor alignment", Physiological Measurement, Institute of Physics Publishing, Bristol, GB, vol. 26, No. 2, Apr. 1, 2005 (Apr. 1, 2005), pp. S263-S278, (16 pages).

Joachimowicz, N.; Mallorqui, J. J.; Bolomey, J. C. and Broquets, A. (1998). "Convergence and stability assessment of Newton-Kantorovich reconstruction algorithms for microwave tomography," IEEE Transactions on Medical Imaging 17 : 562-570. (9 pages).

Jofre, L., et al., "Medical Imaging with a Microwave Tomographic Scanner," IEEE Transactions on Biomedical Engineering (Mar. 1990), pp. 303-312, vol. 37, No. 3 (10 pages).

Kleinman, R. and den Berg, P. (1992). "A modified gradient method for two-dimensional problems in tomography," Journal of Computational and Applied Mathematics 42 : 17-35.

Lobel, P.; Kleinman, R. E.; Pichot, C.; Blanc-Feraud, L. and Barlaud, M. (1996). "Conjugate-Gradient Method for Soliving Inverse Scattering with Experimental Data", IEEE Antennas and Propagation Magazine 38 : 48.

Meaney, P. M.; Paulsen, K. D.; Hartov, A. and Crane, R. K. (1996). "Microwave imaging for tissue assessment: initial evaluation in multitarget tissue-equivalent phantoms", IEEE Transactions on Biomedical Engineering 43 : 878-890. (12 pages).

Yongjie Jessica Zhang et al.: "A New Method to Improve Quality of Reconstructed Images in Tomography". In: "Computational Modeling of Objects Presented in Images. Fundamentals, Methods, and Applications". Jan. 1, 2014 (Jan. 1, 2014), Springer, USA, pp. 267-272.

Poltschak et al., "High precision realtime RF-measurement system for imaging of stroke", 2017 47th European Microwave Conference (EUMC), European Microwave Association, Oct. 10, 2017, pp. 864-867, (4 pages).

Rompelman, O., and H.H. Ros, Coherent averaging technique: A tutorial review Part 1 Noise reduction and the equivalent filter, Journal of biomedical engineering 8, No. 1 (1986): 24-29.

Semenov, S.Y.; Posukh, V.G.; Bulyshev, A. E.; Williams, T.; Clark, P.; Sizov, Y.E.; Souvorov, A. E.; Voinov, B.A.: "Development of Microwave Tomography for Functional Cardiac Imaging." Biomedical Imaging: Macro to Nano, 2004. IEEE International Symposium on Arlington, VA, USA IEEE Apr. 15, 2004 (Apr. 15, 2004), pp. 1351-1353, XP010774114, DOI: 10.1109/ISBI.2004.1398797 ISBN: 978-0-7803-8389-0 (3 pages).

Semenov, S.Y.; Simonova, G. I.; Starostin, A.N.; Taran, M.G.; Souvorov, A.E.; Bulyshev, A.E. Svenson, R.H.; Nazarov, A.G.; Sizov, Y.E.,; Posukh, V.G.; Pavlovsky, A. and Tatsis G.P. (2001) "Dielectrical Model of Cellular Structures in Radio Frequency and Microwave Spectrum. Electrically Interacting Versus Noninteracting Cells." Annals of Biomedical Engineering, vol. 29. pp. 427-435. (8 pages).

Semenov, S. Y.; Bulyshev, A. E.; Abubakar, A.; Posukh, V. G.; Sizov, Y. E.; Souvorov, A. E.; van den Berg, P. M. and Williams, T. C. (2005). Microwave-tomographic imaging of the high dielectric-contrast objects using different imagereconstruction approaches, IEEE Transactions on Microwave Theory and Techniques 53 : 2284-2294. (10 pages).

Semenov, S. Y.; Bulyshev, A. E.; Souvorov, A. E.; Svenson, R. H.; Sizov, Y. E.; Vorisov, V. Y.; Posukh, V. G.; Kozlov, I. M.; Nazarov, A. G. and Tatsis, G. P. (1998). Microwave tomography: theoretical and experimental investigation of the iteration reconstruction algorithm, IEEE Transactions on Microwave Theory and Techniques 46 : 133-141. (9 pages).

Semenov, S. Y.; Bulyshev, A. E.; Posukh, V. G.; Sizov, Y. E.; Williams, T. C. and Souvorov, A. E. (2003). Microwave Tomography for Detection/Imaging of Myocardial Infarction. I. Excised Canine Hearts, Annals of Biomedical Engineering 31 : 262-270. (9 pages).

Semenov, S., et al., "Microwave Tomography of Extremities: 1. Dedicated 2D System and Physiological Signatures," Physics in Medicine and Biology (2011), pp. 2005-2017, vol. 56, No. 7, published by Institute of Physics and Engineering in Medicine, United Kingdom (13 pages).

Semenov, S.Y.: "Microwave tomography: review of the progress towards clinical applications", Philosophical Transactions of the Royal Society, vol. 2009, No. 367, Dec. 31, 2009. pp. 3021-3042, XP002661164. DOI: 10.1098/rsta.2009.0092 *the whole document*. (22 pages).

Semenov, S.Y.; Kellam, J.; Althausen, P.; Williams, T.; Abubakar, A.; Bulyshev, A.; Sizov, Y. (2007) "Microwave tomography for functional imaging of extremity soft tissues: feasibility assessment." Physics in Medicine and Biology, doi: 10.1088/0031-9155/52/18/015. (15 pages).

Semenov, S.Y. et al.: "Myocardial ischemia and infarction can be detected by microwave spectroscopy. II. Biophysical reconstruction", Engineering in Medicine and Biology Society, 1996. Bridging Disciplines for Biomedicine., 18th Annual International Conference

(56) References Cited

OTHER PUBLICATIONS of the IEEE Amsterdam, Netherlands Oct. 31-Nov. 3, NY, NY, IEEE vol. 4 Oct. 31, 1996 pp. 1363-1364, XP010261997, DOI: 10.1109/EMBS. 1996.647455 ISBN:978-0-7803-3811-1.

Souvorov, A. E.; Bulyshev, A. E.; Semenov, S. Y.; Svenson, R. H.; Nazarov, A. G.; Sizov, Y. E. and Tatsis, G. P. (1998). Microwave tomography: a two-dimensional Newton iterative scheme, IEEE Transactions on Microwave Theory and Techniques 46 : 1654-1659. (6 pages).

Yaniv, Ziv, et al. "Electromagnetic tracking in the clinical environment." Medical physics 36.3 (2009): 876-892 (17 pages).

Zhu et al.: "An improved back-projection algorithm for electrical impedance tomography", Automation Congress, 2008. WAC 2008. World, IEEE, Piscataway, NJ, USA, Sep. 28, 2008 (Sep. 28, 2008), pp. 1-4, XP031371153, ISBN: 978-1-889335-38-4.

Zulkarnay et al., "Advancements in Transmitters and Sensors for Biological Tissue Imaging in Magnetic Induction Tomography", Sensors, vol. 12, No. 12, Dec. 29, 2012, pp. 7126-7156, ( 20 pages).

"European Extended Search Report of the European Patent Office" in European Patent Application No. 16856382.3 for EMTensor GmbH, dated Apr. 24, 2019, 7 pages.

"Extended European Search Report," European Patent Application No. 13856581.7, for EMTensor GmbH, et al., dated Aug. 25, 2016 (7 pages).

"International Preliminary Report" and "Written Opinion of the International Searching Authority" (ISA/US) in EMTENSOR GMBH, International Patent Application Serial No. PCT/US2017/063169, dated Jun. 6, 2019 (19 pages).

"International Preliminary Report" and "Written Opinion of the International Searching Authority" (ISA/US) in EMTENSOR GMBH, International Patent Application Serial No. PCT/US2016/057254, dated Apr. 26, 2018 (6 pages).

"International Search Report" and "Written Opinion of the International Searching Authority" (ISA/US) in EMTENSOR GmbH, International Patent Application Serial No. PCT/US2016/057254, dated Jan. 12, 2017 (7 pages).

"Russian Search Report" of Federal Institute of Industrial Property (FIIP) in EMTENSOR GMBH, Russian Patent Application Serial No. 2018117885, dated Feb. 3, 2020 (4 pages).

\* cited by examiner

135

ELECTROMAGNETIC INTERFERENCE PATTERN RECOGNITION TOMOGRAPHY

CROSS REFERENCE TO RELATED APPLICATIONS

The present application is a U.S. continuation patent application of, and claims priority under 35 U.S.C. § 120 to U.S. patent application Ser. No. 15/953,694 to Semenov, filed Apr. 16, 2018 and previously published on Aug. 16, 2018 as U.S. Patent Application Publication No. 2018/0231594 A1 and issued as U.S. Pat. No. 10,921,361 on Feb. 16, 2021, which '694 application, the application publication thereof, and the patent issuing therefrom are each incorporated herein by reference in their entirety, and which '694 application is a U.S. continuation patent application of, and claims priority under 35 U.S.C. § 120 to, International Application No. PCT/US2016/057254, filed Oct. 16, 2016, designating the U.S., and entitled "ELECTROMAGNETIC INTERFERENCE PATTERN RECOGNITION TOMOGRAPHY," which '254 application published as WO 2017/066731 A1 on Apr. 20, 2017, which '254 application and the application publication thereof are each expressly incorporated herein by reference in their entirety, and which '254 application, for purposes of the United States, is a U.S. nonprovisional patent application of, and claims priority under 35 U.S.C. § 119(e) to, U.S. provisional patent application Ser. No. 62/242,915, filed Oct. 16, 2015 and entitled "ELECTROMAGNETIC INTERFERENCE PATTERN RECOGNITION TOMOGRAPHY," which '915 application is expressly incorporated herein by reference in its entirety. In addition, each of the following patents, patent applications and patent application publications is incorporated by reference herein in its entirety:
  (a) U.S. Pat. No. 9,414,749 to Semenov, issued Aug. 16, 2016 and previously published on Jun. 5, 2014 as U.S. Patent Application Publication No. 2014/0155740 A1, which is intended, at least, to provide background and technical information with regard to the systems and environments of the inventions of the current patent application; and
  (b) U.S. Patent Application Publication No. 2012/0010493 A1, which was published Jan. 12, 2012 based on U.S. patent application Ser. No. 13/173,078 to Semenov, filed Jun. 30, 2011 and entitled "SYSTEMS AND METHODS OF ELECTROMAGNETIC TOMOGRAPHY (EMT) DIFFERENTIAL (DYNAMIC) FUSED IMAGING," which is intended to provide background and technical information with regard to 4D EMT imaging.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to electromagnetic tomography, and, in particular, to the use of electromagnetic interference pattern recognition strategies to remove amplified distortions caused by repeated interference patterns.

Background

Electromagnetic tomography (EMT) is a relatively recent imaging modality with great potential for both biomedical and industrial applications. Biomedical applications include but are not limited to the non-invasive assessment of functional and pathological conditions of biological tissues. Industrial applications include but are not limited to oil and gas exploration, mine search and assessment, and flow assessment within non-metallic pipes. Using EMT, objects such as biological tissues are differentiated and, consequentially, can be imaged based on the differences in the dielectric properties of such objects. EMT is believed to have high potential for biomedical applications based on the recent demonstration of the dependency of tissue dielectric properties on the tissue's various functional and pathological conditions, such as blood and oxygen contents, ischemia and infarction malignancies, edema and others.

Two-dimensional (2D), three-dimensional (3D) and even "four-dimensional" (4D) EMT systems and methods of image reconstruction have been developed over the last decade or more. Feasibility of the technology for various biomedical and industrial applications has been demonstrated, for example, for cardiac imaging and extremities imaging.

As in any tomographic imaging, the classical EMT imaging scenario consists of cycles of measurements of complex signals, as affected by the presence of an object under study located within a so-called imaging domain, as produced by a plurality of transmitters located at various points around the object and measured on a plurality of receivers located at various points around the object. This is illustrated in FIG. 1. The locations of the transmitters and receivers may be within the imaging domain, on the boundary of the imaging domain, or outside the imaging domain. As recounted elsewhere herein, the measured matrix of EM signals may then be used in image reconstruction methods in order to reconstruct 3D distribution of dielectric properties of the object 19, i.e., to construct a 3D image of the object. Hardware components disclosed and described in the aforementioned U.S. Pat. No. 9,414,749, can be utilized to generate the necessary EM signals to reconstruct a 3D image of the object 19.

Generally, it is very important for image reconstruction to precisely describe a distribution of an EM field with an imaging domain 21. The distribution of an EM field within an imaging chamber is a very complex phenomenon, even when there is no object of interest inside.

This invention relates to the use of electromagnetic (EM) fields for imaging of the structure of an object 19. The object 19 may be a human body or part of a human body, such as a head, a torso, an arm or the like, but may also be any object without metal shielding. The use of EM fields for imaging inside of a strongly shielded object (but not metallically shielded) is a problem of high complexity. One example of such an application is imaging of the human brain. However, it should be appreciated that other such applications might include imaging of any human tissue that is shielded by a bony structure. The EM imaging of the brain or other tissue surrounded by bone presents a very complicated, high dielectric contrast problem. The challenge is to reconstruct hidden properties of deep brain tissues which are effectively shielded by a high dielectric contrast shield, comprising the skull (with dielectric properties in a range of 16+j5) and the cerebral spinal fluid (with dielectric properties in a range of 60+j30). While this invention, as stated above, is applicable for the imaging of any objects, it is believed to be especially applicable for imaging inside of strongly shielded objects.

EMT imaging of high dielectric contrast objects, including biological objects, possesses the very complicated problem of so-called "diffraction tomography." Devaney A. J. "Current research topics in diffraction tomography", in *Inverse Problems in Scattering and Imaging*, M. BNertero and E. R. Pike, Eds, New York: Adam Hilger, 1992, pp. 47-58. A high dielectric contrast between tissues with high water content, such as but not limited to muscle tissue, and low water content, such as but not limited to bone, presents an additional complication when using EM fields for imaging. Various approaches in 2D and 3D geometries, using scalar and vector approximations, have been developed in an attempt to solve the problem of diffraction tomography. See H. Harada, D. Wall, T. Takenaka, and T. Tanaka, "Conjugate gradient method applied to inverse scattering problem", *IEEE Trans. Antennas and Propagations*, vol. 43, 784-792, August 1995; R. E. Kleinman, and P. M. van den Berg, "A modified gradient method for two-dimensional problems in tomography", *J. Comput. Appl. Math.*, vol. 42, pp. 17-35, January 1992; A. Abubakar, P. M. van den Berg, and J. J. Mallorqui, "Imaging of Biomedical Data Using A Multiplicative Regularized Source Inversion Method," *IEEE Trans. Microwave Theory and Techniques*, v. 50, pp. 1761-1771, July 2002; N. Joachimowicz, J. J. Mallorqui, J. Ch. Bolomey, and A. Brouguetas, "Convergence and stability assessment of Newton-Kantorovich reconstruction algorithms for microwave tomography", *IEEE Trans. Medical Imaging*, vol. 17, pp. 562-570, August 1998; P. Lobel, R. Kleinman, Ch. Pichot, L. Blanc-FHraud, and M. Barlaud "Conjugate Gradient Method for Solving Inverse Scattering with Experimental Data", *IEEE Antennas & Propagation Magazine*, Vol. 38, pp. 48-51, June 1996; W. C. Chew, and Y. M. Wang, "Reconstruction of two-dimensional permittivity distribution using the distorted Born iterative method", *IEEE Trans. Medical Imaging*, vol. 9, p. 218-225, June 1990; P. M. Meaney, K. D. Paulsen, A. Hartov, and R. K. Crane, "Microwave imaging for tissue assessment: Initial evaluation in multitarget tissue equivalent phantoms", *IEEE Trans. Biomedical Engineering*, vol. 43, pp. 878-890, September 1996.

In previous works, mathematical algorithms and their respective systems and software implementations have been developed that proved to be very reliable and delivered images of objects of different sizes from a few centimeters in the excised canine heart up to a full-size body in 2D, 3D and 3D vector cases. See A. E. Souvorov, A. E. Bulyshev, S. Y. Semenov, R. H. Svenson, A. G. Nazarov, Y. E. Sizov, and G. P. Tatsis, "Microwave tomography: A two-dimensional Newton iterative scheme", *IEEE Trans. Microwave Theory and Techniques*, vol. 46, pp. 1654-1659, November 1998; A. E. Bulyshev, A. E. Souvorov, S. Y. Semenov, R. H. Svenson, A. G. Nazarov, Y. E. Sizov, and G. P. Tatsis, "Three-dimensional microwave tomography. Theory and computer experiments in scalar approximation", *Inverse Problems*, vol. 16, pp. 863-875, June 2000; Bulyshev A. E, Souvorov A. E., Semenov S. Y., Posukh V. G., Sizov Y. E. "Three-dimensional Vector Microwave Tomography. Theory and Computational experiments", *Inverse Problems*, 2004, 20, 4, 1239-1259; Semenov S. Y., Bulyshev A. E., Souvorov A. E., Svenson R. H., Sizov Y. E., Borisov V. Y., Posukh V. G., Kozlov I. M., Nazarov A. G., Tatsis G. P. "Microwave Tomography: Theoretical and Experimental Investigation of the Iteration Reconstruction Algorithm", *IEEE Trans MTT*, 1998, 46, 2, 133-141; Semenov S. Y., Bulyshev A. E., Abubakar A., Posukh V. G., Sizov Y. E., Souvorov A. E., Van den Berg P., Williams T. "Microwave tomographic imaging of the high dielectric contrast objects using different imaging approaches", *IEEE Trans. MTT*, v. 53, No 7, pp 2284-2294, 2005; Semenov S. Y., Kellam J. F., Althausen P., Williams T. C., Abubakar A., Bulyshev A., Sizov Y. "Microwave tomography for functional imaging of extremity soft tissues. Feasibility assessment", *Phys. Med. Biol.*, 2007, 52, 5705-5719; Semenov S. Y., Bulyshev A. E., Posukh V. G., Sizov Y. E., Williams T. C., Souvorov A. E. "Microwave tomography for detection/imaging of myocardial infarction. 1. Excised canine hearts", *Annals of Biomedical Engineering*, 2003, 31, 262-270. However, none of above methods cited in these previous works have proven to be effective when imaging inside of strongly shielded objects. A new approach is needed for the accurate representation of EMT imaging of objects that have a high dielectric contrast shield, such as but not limited to the human brain.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

Broadly defined, the present invention according to one aspect is a method of the use of electromagnetic field in such a manner that an electromagnetic interference picture is generated within an imaging domain, revealing the superposition of 3D dielectric structure of an object together with electromagnetic interference pattern, while electromagnetic interference pattern was further recognized and applied to a 3D electromagnetic superposition, nullifying or diminishing electromagnetic interference pattern and revealing 3D dielectric structure of an object.

Broadly defined, the present invention according to another aspect is a method of 4D dynamic fused electromagnetic pattern recognition tomography.

Broadly defined, the present invention according to another aspect is a method of monitoring of viability and functional conditions of biological tissue utilizing 4D dynamic fused electromagnetic recognition tomography.

Broadly defined, the present invention according to another aspect is an electromagnetic Interference Pattern Recognition Tomography (EMIPRT) method for use in an image reconstruction system, as shown and described.

Broadly defined, the present invention according to another aspect is an Electromagnetic Interference Pattern Recognition Tomography (EMIPRT) method for use in an image reconstruction system, comprising: via an electromagnetic tomography system, generating electromagnetic field data corresponding to an object in an imaging domain, wherein the electromagnetic field data is measured at a plurality of receivers after being produced at a plurality of transmitters and interacting with the object; and using the generated electromagnetic field data, repeatedly, in a recursive manner: forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image.

In a feature of this aspect, the step of forming a disturbed electromagnetic interference image based at least in part on the undisturbed electromagnetic interference image includes forming a disturbed electromagnetic interference image based at least in part on determination of an object factor that is a function of the differences between experimentally electromagnetic fields and electromagnetic fields calculated during the step of forming an undisturbed electromagnetic interference image. In further features, the object factor is determined as $$\frac{\left(\overline{E}_{ij}^{Sim} - \overline{E}_{ij}^{Exp}\right)}{\overline{M}_{ij}},$$

where $Ez_{ij}^{Sim\ or\ Exp}$ is the experimentally simulated or measured value, respectively, of the z-component of the electromagnetic field measured by receiver j when transmitter i is the source of the electromagnetic field, where $\overline{M}_{ij}$ is presented in a general form as $\alpha * f(E_{ij}^{Exp}) + \beta * (\Sigma_{ij} \overline{E}_{ij} * \Sigma_{ij} E_{ij}) + \gamma * \Omega$, where $\alpha, \beta$ and $\gamma$ are coefficients of real non-zero or zero values, where $\Omega$ is a regularization operator, and where $f(E_{ij}^{Exp})$ is a function of its argument; the object factor is determined as $$\frac{\left(Ez_{ij}^{Sim} - Ez_{ij}^{Exp}\right)}{\max\left\|\left(Ez_{ij}^{Exp}\right)\right\|},$$

where $Ez_{ij}^{Sim\ or\ Exp}$ is the experimentally simulated or measured value, respectively, of the z-component of the electromagnetic field measured by receiver j when transmitter i is the source of the electromagnetic field, and where $\max\|Ez_{ij}^{Exp}\|$ is the maximal norm of the experimentally measured z-component of the electromagnetic field; the object factor is determined as $$\frac{\left(Ez_{ij}^{Sim} - Ez_{ij}^{Exp}\right)}{\left\|\left(Ez_{ij}^{Exp}\right)\right\|^{\theta}},$$

where $Ez_{ij}^{Sim\ or\ Exp}$ or Exp is the experimentally simulated or measured value, respectively, of the z-component of the electromagnetic field measured by receiver j when transmitter i is the source of the electromagnetic field, and where $\|Ez_{ij}^{Exp}\|^{\theta}$ is the norm of the experimentally measured z-component of the electromagnetic field measured by receiver j when transmitter i is the source of the electromagnetic field in power of θ; the step of forming a disturbed electromagnetic interference image includes calculation of $\Sigma_{k=1,N} W_k \Sigma_{i=1=N;\ j=1,M} \overline{E_i(f_k,x,y,z)} * \overline{E_j(f_k,x,y,z)} *$ Object Factor$_{i,j}(f_k)$, where $\overline{E_{i=1toN}(f_k,x,y,z)}$ and $\overline{E_{j=1toM}(f_k,x,y,z)}$ are 3D electromagnetic fields (x,y,z) distribution from electromagnetic sources of frequency $f_k$ located at the positions of physical sources (from 1 to N) in the electromagnetic tomography system and at the position of physical receivers (from 1 to M) correspondingly, taken as conjugate values, and wherein Object Factor$_{i,j}$ is the "ij"$^{th}$ component of the object factor, from transmitter i to receiver j; the step of recognizing electromagnetic interference patterns in the repeatedly formed disturbed electromagnetic interference images includes the calculation of sums $\Sigma_{k=1,N}$ $W_k \Sigma_{i=1=N;\ j=1,M} \overline{E_i(f_k,x,y,z)} * \overline{E_j(f_k,x,y,z)} *$ Object Factor$_{i,j}(f_k)$ where $\overline{E_{i=1toN}(f_k,x,y,z)}$ and $\overline{E_{j=1toM}(f_k,x,y,z)}$ are 3D electromagnetic fields (x,y,z) distribution from electromagnetic sources of frequency $f_k$ located at the positions of physical sources (from 1 to N) in the electromagnetic tomography system and at the position of the physical receivers (from 1 to M) correspondingly, taken as conjugate values, and wherein Object Factor$_{i,j}$ is the "ij"$^{th}$ component of the object factor, from transmitter i to receiver j; and/or wherein the step of recognizing electromagnetic interference patterns in the repeatedly formed disturbed electromagnetic interference images includes the calculation, for iteration i>1, $$\sum_{i=1,N;j=1,M}^{at\ iteration\ i} \overline{E_i(x,y,z)} * \overline{E_j(x,y,z)} * \text{Object Factor}_{i,j} -$$

$$\alpha * \left(\varepsilon^{i-1}(\vec{r}) - \varepsilon_{bkgd}\right) * \sum_{i=1,N;j=1,M}^{at\ iteration\ i-1} \overline{E_i(x,y,z)} * \overline{E_j(x,y,z)} * \text{Object Factor}_{i,j} -$$

$$\left(\varepsilon^{i-1}(\vec{r}) - \varepsilon_{bkgd}\right)$$

where for simplicity the frequency terms are omitted, where $\overline{E_{i=}(x,y,z)}$ and $\overline{E_{j=}(x,y,z)}$ are 3D electromagnetic fields (x,y,z) distribution from electromagnetic sources located at the positions of physical sources (from 1 to N) in the electromagnetic tomography system and at the position of the physical receivers (from 1 to M) correspondingly, taken as conjugate values, and wherein Object Factor$_{i,j}$ is the "ij"$^{th}$ component of the object factor, from transmitter i to receiver j.

In another feature of this aspect, the method further includes a step, carried out after each repeated step of forming a superposition image, of determining whether a convergence objective has been reached.

In another feature of this aspect, the method is used as part of a method of generating 4D differential (dynamic) fused images. In further features, generating 4D differential (dynamic) fused images includes combining at least one successively-formed images indicating relative physiological change with a baseline anatomical image for display as a single unified image; and/or the method of generating 4D differential (dynamic) fused images is used as part of a method of monitoring viability and/or functional conditions of biological tissue utilizing 4D dynamic fused electromagnetic pattern recognition tomography.

In another feature of this aspect, the steps of forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image are carried out sequentially.

In another feature of this aspect, the method further includes a step of displaying the superposition image via a display unit.

Broadly defined, the present invention according to another aspect is a method of reconstructing an image using electromagnetic interference pattern recognition tomography, including: via an electromagnetic tomography system, generating electromagnetic field data corresponding to an object in an imaging domain, wherein the electromagnetic field data is measured at a plurality of receivers after being produced at a plurality of transmitters and interacting with the object; and using the generated electromagnetic field data, repeatedly, in a recursive manner: forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image.

In a feature of this aspect, the step of forming a disturbed electromagnetic interference image based at least in part on the undisturbed electromagnetic interference image includes forming a disturbed electromagnetic interference image based at least in part on determination of an object factor that is a function of the differences between experimentally electromagnetic fields and electromagnetic fields calculated during the step of forming an undisturbed electromagnetic interference image.

In another feature of this aspect, the method further includes a step, carried out after each repeated step of forming a superposition image, of determining whether a convergence objective has been reached.

In another feature of this aspect, the method is used as part of a method of generating 4D differential (dynamic) fused images. In further features, generating 4D differential (dynamic) fused images includes combining at least one successively-formed images indicating relative physiological change with a baseline anatomical image for display as a single unified image; and/or the method of generating 4D differential (dynamic) fused images is used as part of a method of monitoring viability and/or functional conditions of biological tissue utilizing 4D dynamic fused electromagnetic pattern recognition tomography.

In another feature of this aspect, the steps of forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image are carried out sequentially.

In another feature of this aspect, the method further includes a step of displaying the superposition image via a display unit.

Broadly defined, the present invention according to another aspect is an image reconstruction system using electromagnetic interference pattern recognition tomography, including: an electromagnetic tomography system that generates electromagnetic field data corresponding to an object in an imaging domain, the electromagnetic tomography system having a plurality of electromagnetic transmitters, a plurality of receivers that measure the electromagnetic data after being produced at the plurality of transmitters and interacting with the object, and a boundary apparatus; and a processing center that, using the generated electromagnetic field data, repeatedly, in a recursive manner: carries out steps of forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image.

In a feature of this aspect, the step of forming a disturbed electromagnetic interference image based at least in part on the undisturbed electromagnetic interference image includes forming a disturbed electromagnetic interference image based at least in part on determination of an object factor that is a function of the differences between experimentally electromagnetic fields and electromagnetic fields calculated during the step of forming an undisturbed electromagnetic interference image.

In another feature of this aspect, the processing center further carries out a step, carried out after each repeated step of forming a superposition image, of determining whether a convergence objective has been reached.

In another feature of this aspect, the steps carried out by the processing center are used as part of a method of generating 4D differential (dynamic) fused images. In further features, generating 4D differential (dynamic) fused images includes combining at least one successively-formed images indicating relative physiological change with a baseline anatomical image for display as a single unified image; and/or the method of generating 4D differential (dynamic) fused images is used as part of a method of monitoring viability and/or functional conditions of biological tissue utilizing 4D dynamic fused electromagnetic pattern recognition tomography.

In another feature of this aspect, the steps of forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image are carried out sequentially.

In another feature of this aspect, the method further includes a display unit that displays the superposition image.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
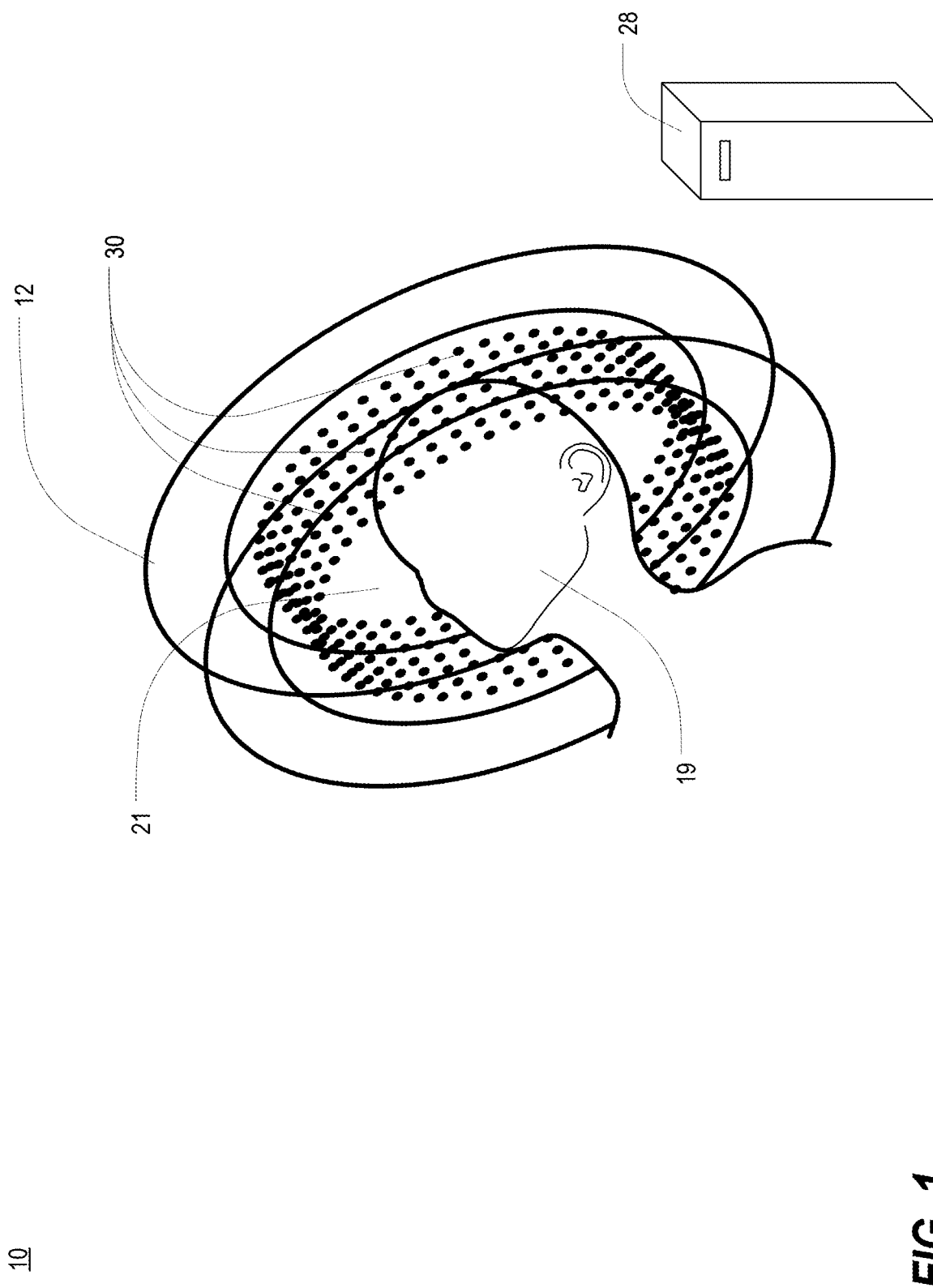
FIG. 1 is a simplified schematic illustration of portions of an electromagnetic tomography (EMT) system.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term-differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

FIG. 1 is a simplified schematic illustration of portions of an electromagnetic tomography (EMT) system 10. In the system 10, a boundary apparatus 12 surrounds an imaging domain 21. An object 19 (in this example, a human head) is placed in the imaging domain 21. A plurality of EM hardware devices 30, usually but not necessarily always disposed on the boundary apparatus 12, act as transmitters (sources) and/or receivers. (As described herein, the hardware devices 30 are generally considered to act as both transmitters and receivers, but it will be appreciated that transmitters and receivers that are separate from each other may additionally or alternatively be utilized.) A computer system 28 serves as a processing center where initial data is pre-processed and images are reconstructed and post-processed. In at least some embodiments, the EMT system 10 further includes a background or matching fluid or other media. The matching media is a solution or gel that is needed or useful inside the imaging domain when the object 19 is being imaged in order to address electromagnetic body-matching problems and/or other issues. In at least some embodiments, the computer system 28 and its data processing functionality and imaging software is directly connected to the EM field transmitting/receiving hardware devices 30, while in other embodiments some or all of the computer system 28 is remotely connected through wireless technology and/or high speed wire connections. Functionally, much of the operation of the EMT system 10 may be similar to that described in the aforementioned U.S. Pat. No. 9,414,749 but various particular embodiments and features may be described herein.

Figure 2:
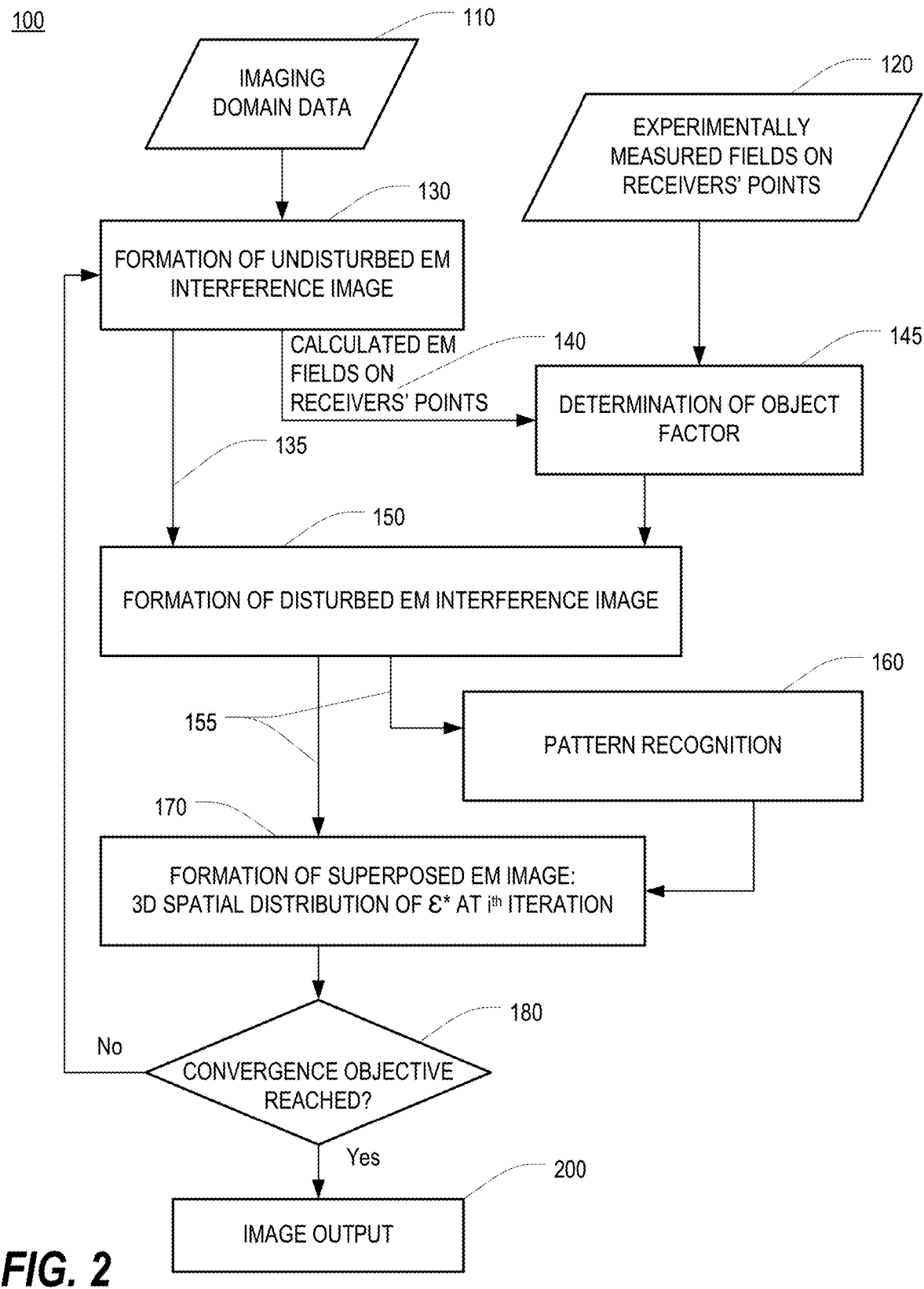
FIG. 2 is a flow diagram of an EM Interference Pattern Recognition Tomography (EMIPRT) method for use in an image reconstruction system in accordance with one or more preferred embodiments of the present invention.

As described above, EMT imaging of high dielectric contrast objects, including biological objects, involves the very complicated problem of so-called "diffraction tomography." A high dielectric contrast between tissues with high water content, such as but not limited to muscle tissue, and low water content, such as but not limited to bone, presents an additional complication when using EM fields for imaging. FIG. 2 is a flow diagram of an EM Interference Pattern Recognition Tomography (EMIPRT) method 100 for use in an image reconstruction system in accordance with one or more preferred embodiments of the present invention. The EMIPRT method 100 may be carried out using EM fields data generated using some or all of the elements of the EMT system 10 described briefly with regard to FIG. 1.

The EMIPRT method 100 is an iterative process where a convergence check (shown at step 180) occurs after each iteration through the various image formation processes until suitable results are obtained and provided as the image output 200. Primary inputs to the EMIPRT method 100 are imaging domain data 110 and experimentally measured EM data 120. The imaging domain data 110 includes the spatial location of the source EM field hardware devices 30 at a plurality of spatial locations and at $k^{th}$ frequencies (k from 1 to K) ($E_{i=1\ to\ N}(f_{k=1\ to\ K})$) and the receiver EM field hardware devices 30 at a plurality of spatial locations and at $k^{th}$ frequencies (k from 1 to K) ($E_{j=1\ to\ M}(f_{k=1\ to\ K})$) with respect to the imaging domain 21, where N is the number of source EM field devices 30 and M is the number of receiver EM field devices 30. The imaging domain data 110 also includes the dielectric properties of a matching media ($\varepsilon_0$) within an imaging domain 21, and may also include other environmental or physical information/data. The experimentally measured EM data 120 is a matrix containing experimentally measured EM fields (for example as in amplitude, phase and polarization form or as real, imaginary and polarization form) on receivers' points, represented as {$\overline{E}_{ij}^{Exp}(f_k)$}. EM fields receivers' points may be associated with any or all of the EM field devices 30.

At block 130, an "undisturbed" EM interference image is formed. In the initial pass, formation of the undisturbed EM interference image (shown as an output 135 of the undisturbed image formation block 130) is obtained based only on the imaging domain data 110 of the EMIPRT method 100. In subsequent iterations, formation of the undisturbed interference image preferably also uses a spatial distribution of dielectric properties within the imaging domain 21. Depending on the application, the spatial distribution may be a 2D spatial distribution or a 3D spatial distribution. In at least some embodiments, the 3D spatial distribution of dielectric properties is described as $\varepsilon^*(x,y,z)$ in the Cartesian coordinate system and is obtained during a previous iteration in a superposition image formation block 170, described below. The 3D spatial distribution of dielectric properties $\varepsilon^*(x,y,z)$ may be characterized as an image of the study object 19 in dielectric scale.

Figure 3:
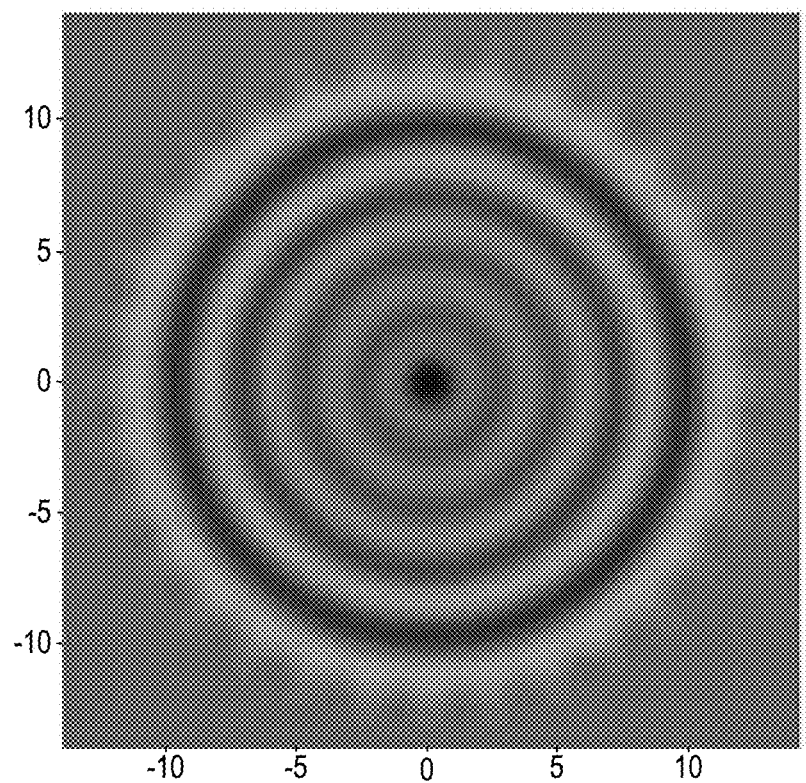
FIG. 3 is an exemplary undisturbed EM interference image for an imaging domain designed for human head imaging.

The task of the undisturbed EM interference image formation block 130 is to synthesize a 2D or 3D interference image (picture) 135 from the plurality of EM sources/receivers 30 located within or on the boundary of an imaging domain 21. During the image formation process, all EM field devices 30 (i=1 to N and j=1 to M) are considered as sources of the EM field. The determination of the (3D) undisturbed EM interference image 135 is generated from the following function:

$$\sum_{k=1,N} W_k \sum_{i=1,N; j=1,M} E_i(f_k, x, y, z) * E_j(f_k, x, y, z) \quad (1)$$

where $E_{i=1\ to\ N}(f_k,x,y,z)$ and $E_{j=1\ to\ M}(f_k,x,y,z)$ are the 3D EM fields (x,y,z) distribution within the imaging domain 21 from the EM field devices 30 of probing frequency $f_k$ located at the position of the physical sources (from 1 to N) and at the position of the physical receivers (from 1 to M) correspondingly, and where $W_k$ is the frequency weight function, which accounts for the different input of frequency dependent EM interference images into the function (1). FIG. 3 is an exemplary undisturbed EM interference image 135 for an imaging domain 21 designed for human head imaging. The image 135 was obtained at a specific frequency, which in this case was 1 GHz. The image is a 2D cross-sectional view in the X-Y plane wherein the X and Y scales are in centimeters.

Returning to FIG. 2, the next major operation in the EMIPRT method 100 is the determination of an object factor, as shown at block 145, to be applied to the EM interference image. The object factor is preferably a function of the differences between measured (from block 120) and simulated (from block 130) EM fields for each pair of transmitting (i=1 to N) to receiving (j=1 to M) devices 30 at a certain probing frequency. Thus, the primary inputs to the object factor determination block 145 are the second of the two main inputs to the method 100 (experimentally measured EM fields on receivers' points 120, described previously) and input data 140 (calculated or simulated EM Fields on the receivers' points) generated from the undisturbed EM interference image formation block 130. These two main inputs into the object factor determination block 145 are matrices of data. The first matrix contains experimentally measured EM fields, represented as {$\overline{E}_{ij}^{Exp}(f_k)$}, and the second matrix contains simulated EM fields, represented as {$\overline{E}_{ij}^{Sim}(f_k)$}, where in both cases E is a complex vector value representing electrical (E) and/or magnetic (H) components of the EM field. These values might be presented as a complex (real and imaginary parts) value of each vector component of E and/or H field or scalar value of E and/or H field. They also might be presented as amplitude and/or phase of each vector component of E and/or H field or scalar value of E and/or H field. In at least one embodiment of the present invention, the object factor might be presented in general terms as follows:

$$\frac{(\overline{E}_{ij}^{Sim} - \overline{E}_{ij}^{Exp})}{\overline{M}_{ij}} \quad (2)$$

where $Ez_{ij}^{Sim\ or\ Exp}$ is the experimentally simulated or measured value, respectively, of the z-component of the EM field measured by receiver j when transmitter i is the source of the EM field, where $\overline{M}_{ij}$ is presented in a general form as:

$$\alpha * f(E_{ij}^{Exp}) + \beta * (\Sigma_i \overline{E}_{ij} * \Sigma_j E_{ij}) + \gamma * \Omega \quad (3)$$

where $\alpha, \beta$ and $\gamma$ are coefficients of real non-zero or zero values, $\Omega$ is a regularization operator, and where $f(E_{ij}^{Exp})$ is a function of its argument.

In other embodiments of the present invention, the object factor may have a different composition. This will affect the EM interference image and its pattern. One example of an alternative object factor is presented below for $\alpha=1$, $\beta=0$ and $\gamma=0$:

$$\frac{\left(Ez_{ij}^{Sim} - Ez_{ij}^{Exp}\right)}{\max\|\left(Ez_{ij}^{Exp}\right)\|} \quad (4)$$

where $Ez_{ij}^{Sim \ or \ Exp}$ is the experimentally simulated or measured value, respectively, of the z-component of the EM field measured by receiver j when transmitter i is the source of the EM field, and where $\max\|Ez_{ij}^{Exp}\|$ is the maximal norm of the experimentally measured z-component of the EM field. Another example of an alternative object factor 145 is presented below for $\alpha=1$, $\beta=0$ and $\gamma=0$:

$$\frac{\left(Ez_{ij}^{Sim} - Ez_{ij}^{Exp}\right)}{\|\left(Ez_{ij}^{Exp}\right)\|^{\theta}} \quad (5)$$

where $Ez_{ij}^{Sim \ or \ Exp}$ is the experimentally simulated or measured value, respectively, of the z-component of the EM field measured by receiver j when transmitter i is the source of the EM field, and where $\|Ez_{ij}^{Exp}\|^{\theta}$ is the norm of the experimentally measured z-component of the EM field measured by receiver j when transmitter i is the source of the EM field in power of $\theta$. The power of $\theta$ might, for example, have value of 1 or 2 or 3 or ½ or even some other value.

Output from the object factor determination block 145 and output from the undisturbed EM interference image formation block 130 (i.e., the 2D or 3D undisturbed EM interference image 135) are used in the formation of the disturbed EM interference image, as shown at block 150. The image generated in block 150 is a 2D or 3D image, depending on the application. Formation of the (3D) disturbed EM interference image in the imaging domain 21, as shown at block 150, includes the calculation of sums as shown, for example, in equation (6):

$$\sum_{k=1,N} W_k \sum_{i=1,N; j=1,M} \overline{E_i(f_k, x, y, z)} * \overline{E_j(f_k, x, y, z)} * \text{Object Factor}_{i,j}(f_k) \quad (6)$$

where $\overline{E_{i=1 to N}(f_k,x,y,z)}$ and $\overline{E_{j=1 to M}(f_k,x,y,z)}$ are 3D EM fields (x,y,z) distribution from EM sources 30 of frequency $f_k$ located at the positions of the physical sources (from 1 to N) and at the position of the physical receivers (from 1 to M) correspondingly, taken as conjugate values, and Object Factor$_{i,j}$ is "ij"$^{th}$ component of the chosen object factor, from transmitter i to receiver j, as determined at block 145.

Figure 4A:
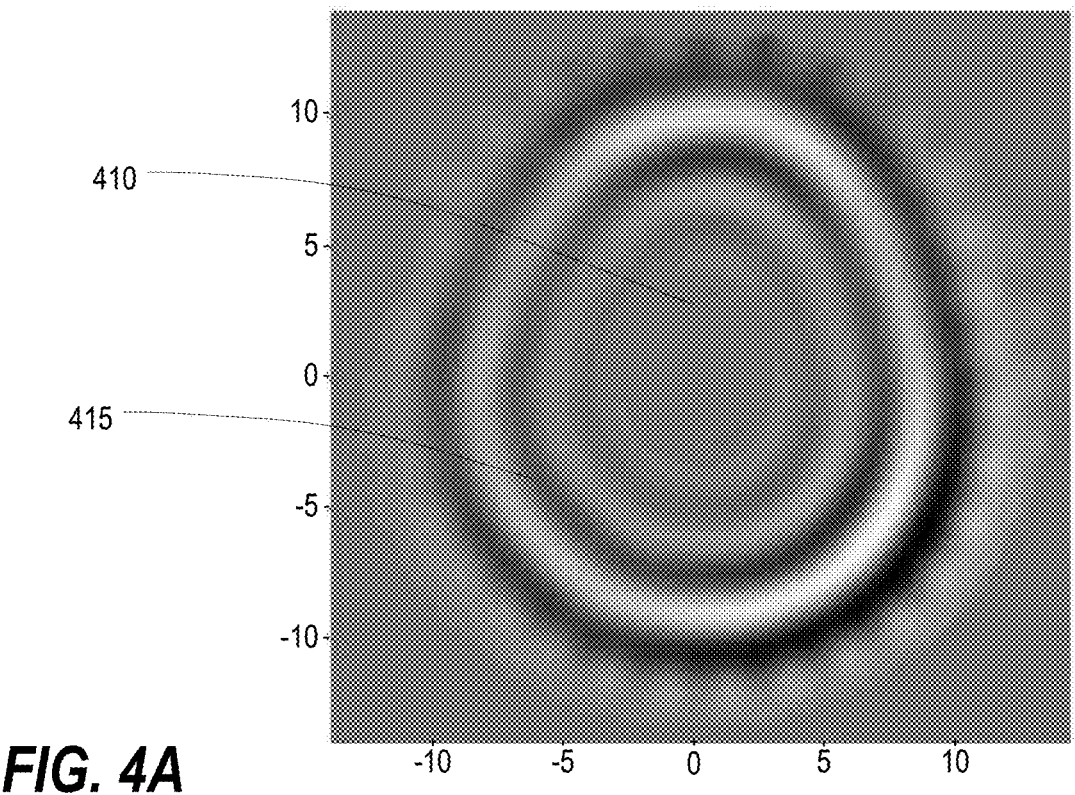
FIGS. 4A and 4B are exemplary disturbed EM interference images for two human head cases.
Figure 4B:
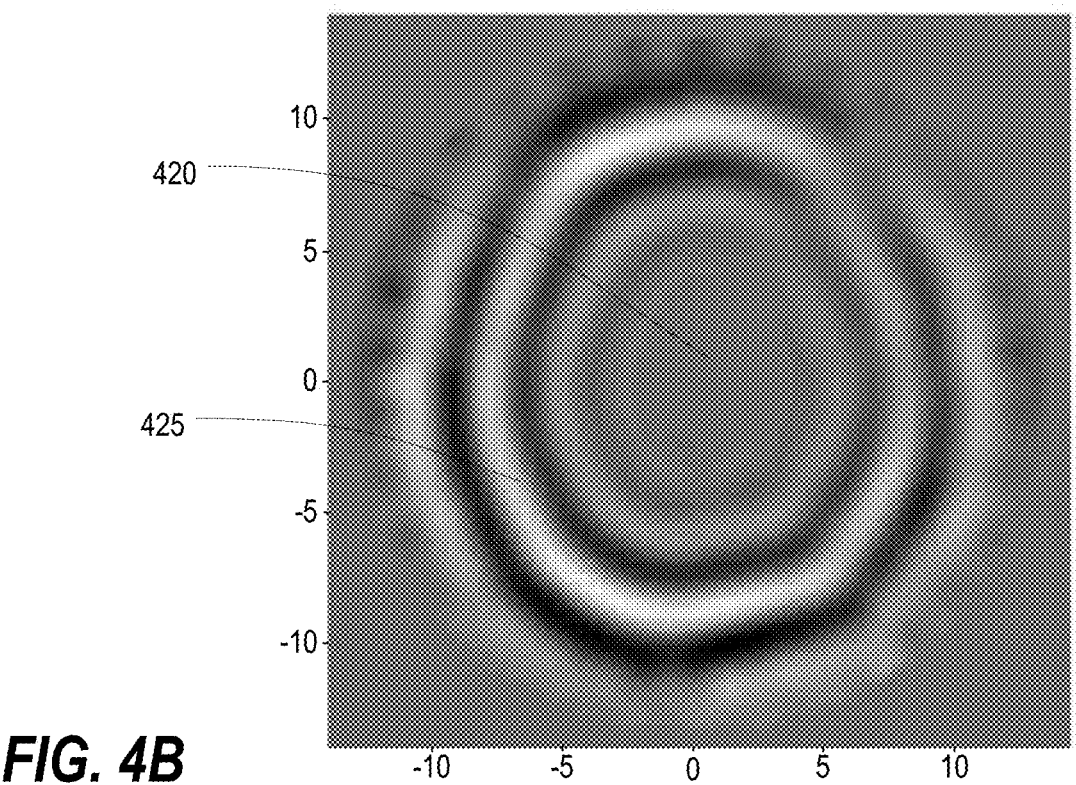

The output of the disturbed EM interference image formation block 150 is a disturbed EM interference image 155 (or data representative thereof). In this regard, FIGS. 4A and 4B are exemplary disturbed EM interference images 155 for two human head cases. Each image 155 is a 2D cross-sectional view in the X-Y plane wherein the X and Y scales are in centimeters. (It will be appreciated that although FIGS. 4A and 4B are 2D illustrations, 3D images may be achieved through further application of the same process.) The alternative object factor shown at (4) was used for these two examples. When comparing the undisturbed EM image 135 of FIG. 3 and the disturbed EM images 155 of FIGS. 4A and 4B, the superposition of a dielectric structure of an object 410,420 (X-Y cross-section of a human head) together with an EM interference pattern 415,425 is clearly seen in FIGS. 4A and 4B, wherein the outermost dark ring in each illustration represents the human skull, and the topologically similar patterns inside such dark ring are remaining EM interference patterns.

After the formation of the disturbed EM interference image in block 150, the image (data) 155 is sent both to a pattern recognition block 160 and to the superposition image formation block 170. The interference pattern recognition and its application work as a two-stage process, wherein stage 1 is the pattern recognition itself and stage 2 is the application of a recognized pattern to a 2D or 3D EM superposition image, nullifying or diminishing the EM interference pattern and revealing a 2D or 3D dielectric structure of the object 19. Those two stages are represented in FIG. 2 by the pattern recognition block 160 and the superposition image formation block 170.

Figure 5:
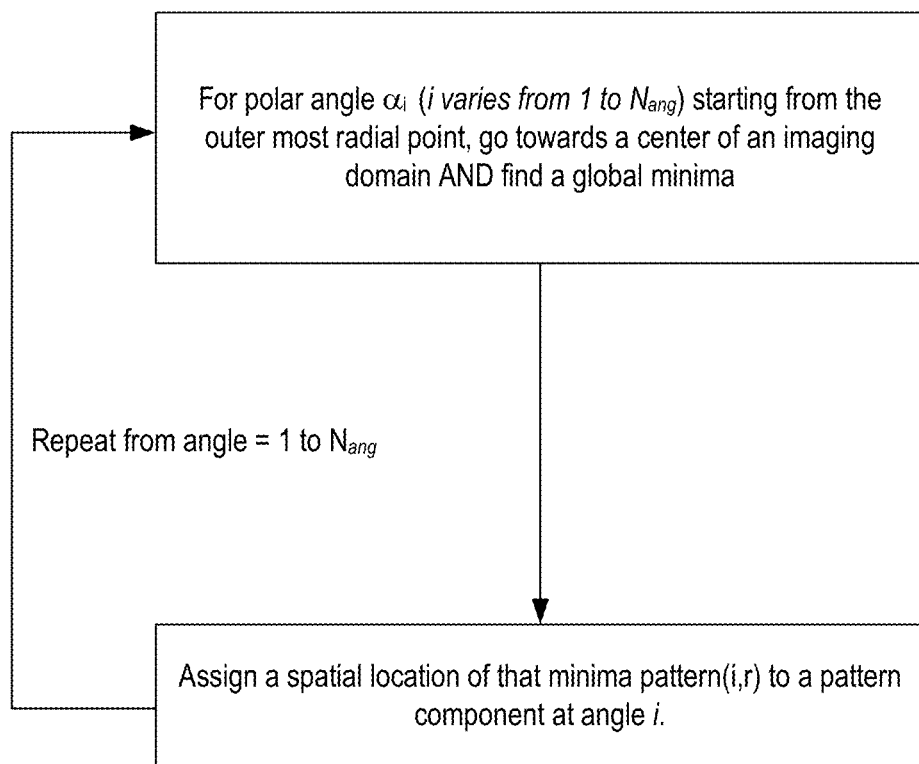
FIG. 5 is a flow diagram of one pattern recognition strategy and set of equations for the pattern recognition block shown in FIG. 2.

Various pattern recognition approaches may be utilized. For example, FIG. 5 is a flow diagram of one pattern recognition strategy 500 and set of equations for the pattern recognition block 160 shown in FIG. 2. A 2D example is used in FIG. 5, but it will be appreciated that such pattern recognition may be applied across multiple X-Y cross-sections to create a 3D image. As shown in FIG. 5, An alternative pattern recognition strategy, sometimes referred to hereinafter as "2ndT optimization," advantageously allows for the development of much sharper patterns in the initial or first iteration of the superposition image formation block 170 and, as a consequence, makes pattern recognition easier on subsequent iterations. The key feature of 2ndT optimization is to use the generalization of (6) at iteration i>1 for the formation of the superposition image (where for simplicity the frequency terms are omitted):

$$\sum_{i=1,N; j=1,M}^{at\ iteration\ i} \overline{E_i(x, y, z)} * \overline{E_j(x, y, z)} * \text{Object Factor}_{i,j} - \quad (7)$$

$$\alpha * \left(\varepsilon^{i-1}(\vec{r}) - \varepsilon_{bkgd}\right) *$$

$$\sum_{i=1,N; j=1,M}^{at\ iteration\ i-1} \overline{E_i(x, y, z)} * \overline{E_j(x, y, z)} * \text{Object Factor}_{i,j} - \left(\varepsilon^{i-1}(\vec{r}) - \varepsilon_{bkgd}\right)$$

In some embodiments, the coefficient $\alpha$ may be independent from the iteration number (and might be found by trial methods), while in other embodiments it may have an iteration-dependent value which helps to speed up the convergence process. In the latter case, one possible strategy is to have a value of coefficient $\alpha$ at iteration i+1 as the maximal absolute difference between the image at iteration i and the image at iteration i−1:

$$\max\|\varepsilon(x,y,z)_i - \varepsilon(x,y,z)_{i-1}\|. \quad (8)$$

In other embodiments of the present invention, other pattern recognition strategies and/or algorithm to find optimal coefficient $\alpha$ might be used.

In some embodiments, the same pattern recognition strategy/procedure may be performed during every iteration of the method 100, while in other embodiments, the pattern recognition strategy/procedure may be dynamically updated after each successive iteration.

The output from the pattern recognition block 160 and the output from the disturbed EM interference image formation block 150 (i.e., the disturbed EM interference image 155)

are provided to the superposition image formation block 170. Superposition image formation 170 may be done by recognizing the patterns via block 160, comparing them to the disturbed EM interference images 155, and then doing pattern corrections. In block 170 the data is analyzed to diminish or nullify the EM interference pattern and reveal the true 2D or 3D structure of an object 19, represented as the image output 200.

Figure 6:
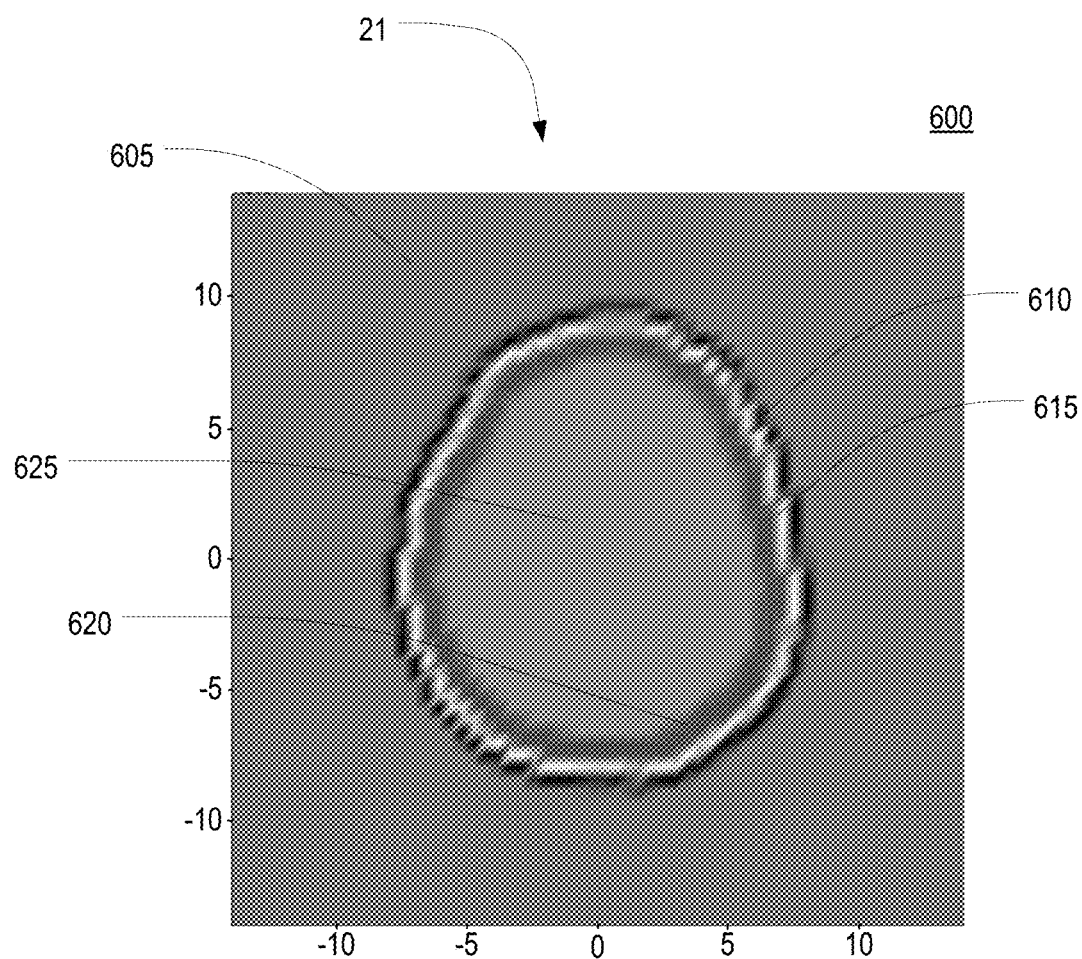
FIG. 6 is an image illustrating the subdivision of the imaging domain into sub-domains.
Figure 7:
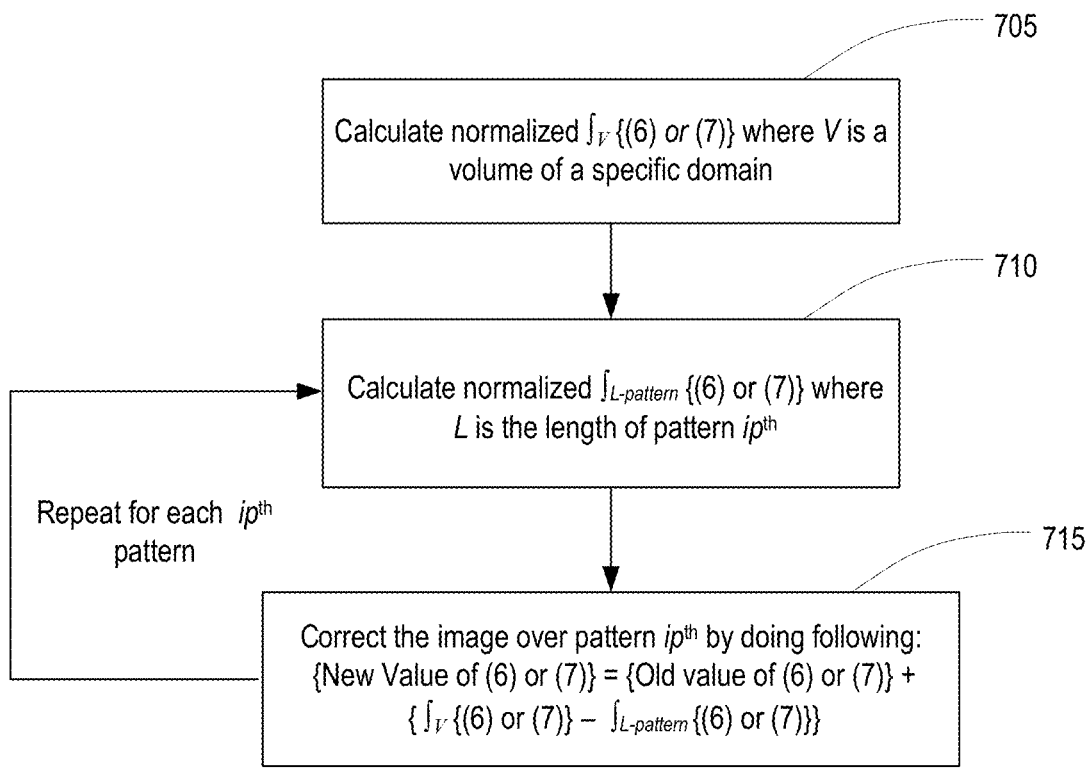
FIG. 7 is a flow diagram of one possible pattern correction strategy that may be carried out in the superposition image formation block for each of a plurality of sub-domains.

Pattern correction may be carried out as follows. First, in at least some embodiments of the method 100, the whole imaging domain 21 may subdivided into a number of characteristic imaging sub-domains. In this regard, FIG. 6 is an image 600 illustrating the subdivision of the imaging domain 21 into sub-domains. More particularly, using the example of a human head as the object 19, the imaging domain 21 may subdivided into an outer (external) domain 605, a skull domain 610, a cerebrospinal fluid (CSF) domain 615, a gray matter domain 620, and a white matter domain 625. FIG. 7 is a flow diagram of one possible pattern correction strategy 700 that may be carried out in the superposition image formation block 170 for each sub-domain. At step 705, a normalized $\int_V$ {value of (6) or (7)} is calculated, where V is a volume of the specific sub-domain. At step 710, a normalized $\int_{L\text{-}pattern}$ {value of (6) or (7)} is calculated, where L is the length of the "ip"$^{th}$ pattern. The logic of step 710 might be easy understood with reference FIG. 3. It can be appreciated that there are clear circular patterns. The number of those circular patterns Np is equal to the number of grids over a radius. Thus, for simple circular patterns like those in FIG. 3, the integration at step 710 is conducted over each pattern ("ip"$^{th}$ pattern) from 1 to Np over the length of $2\pi R_{Np}$. Similarly, for more complex object patterns (for example, the somewhat annular patterns presented in FIGS. 4A and 4B), step 710 involves the calculation of a normalized $\int_{L\text{-}pattern}$ {value of (6) or (7)}, where L is the length of the "ip"$^{th}$ pattern. Then at step 715, the image over the ip$^{th}$ pattern is corrected by setting the new value of (6) or (7) equal to the sum of the old value and $\{\int_V \{(6) \text{ or } (7)\} - \int_{L\text{-}pattern} \{(6) \text{ or } (7)\}\}$. Steps 710 and 715 are then repeated for each ip$^{th}$ pattern.

It will be appreciated that the pattern correction strategy shown in FIG. 7 is not the only pattern correction strategy that may be utilized; other pattern correction strategies may additionally or alternatively be utilized without departing from the scope of the present invention.

After each iteration through block 170, the output is evaluated against a "convergence objective" at step 180. When the convergence objective, the final output image 200 is generated.

Figure 8A:
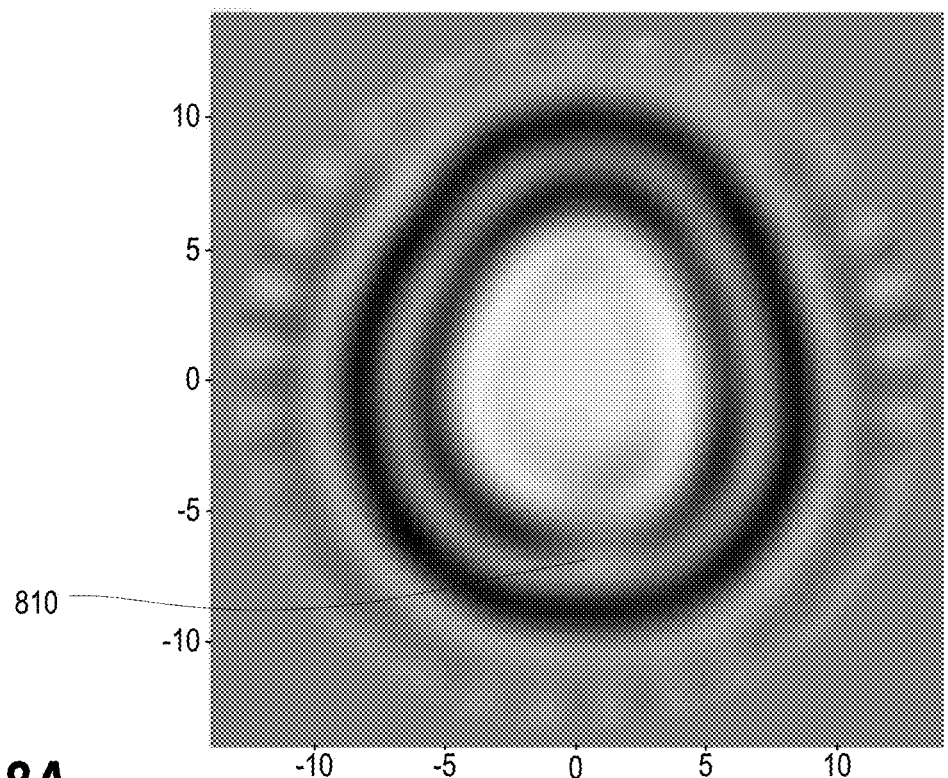
FIG. 8A is an exemplary output image of a virtual stroke victim's head from an iterative imaging method similar to the method of FIG. 2, but where the pattern recognition block and its output information are not used during the image formation.
Figure 8B:
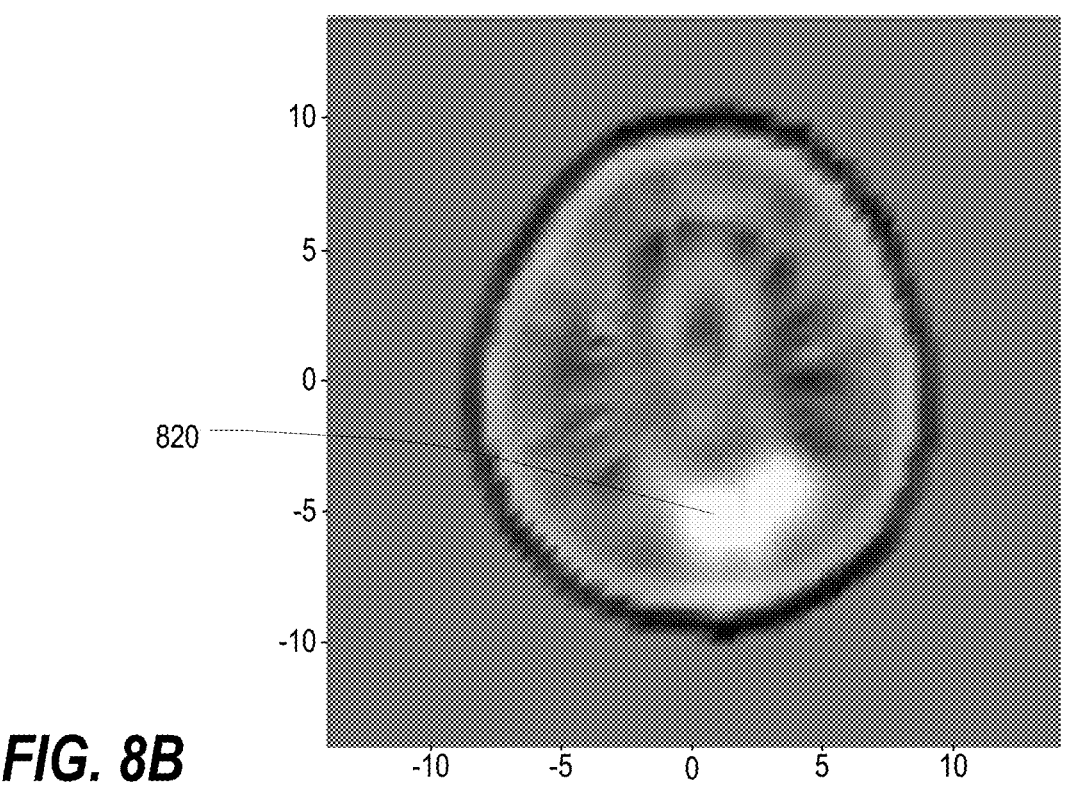
FIG. 8B is an exemplary output image of the same virtual stroke victim's head as that of FIG. 8A, but where the pattern recognition block and its output information are used during the superposition image formation block.

An important benefit of the incorporation of the pattern recognition technology presented herein may be understood as follows. As the iterative process presented in FIG. 2 progresses, the influence of EM interference patterns tends to significantly distort the resulting images of the target 2D or 3D dielectric structure. This is because of the amplification of such a pattern by similar EM interference patterns obtained on the following iterations and the resulting distortion in images produced thereby. In this regard, FIG. 8A is an exemplary output image of a virtual stroke victim's head 19 from an iterative imaging method similar to the method 100 of FIG. 2, but where the pattern recognition block 160 and its output information are not used during the image formation, while FIG. 8B is an exemplary output image 200 of the same virtual stroke victim's head 19 as that of FIG. 8A, but where the pattern recognition block 160 and its output information are used during the superposition image formation block 170. FIG. 8B clearly reveals the virtual stroke area 820 at right bottom of the image. The image in FIG. 8A, obtained without the interference pattern recognition block 160 and its application in block 170, reveals some image distortion within the virtual stroke area 810, but without greater clarity it can only be speculated that the distortion indicates an area of stroke.

It will also be appreciated that although the methodology (including variations and permutations) described herein has been described mostly in terms of 2D and 3D imagery, it is believed equally applicable to 4D EMT technology (3D in space plus 1D in time), wherein 4D dynamic fused electromagnetic tomographic images are generated as described, for example, in the U.S. patent application Ser. No. 13/173,078, the entirety of which has been incorporated herein by reference.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. An image reconstruction system using electromagnetic interference pattern recognition tomography, comprising:
   an electromagnetic tomography system that generates electromagnetic field data corresponding to an object in an imaging domain, the electromagnetic tomography system including:
      a plurality of electromagnetic transmitters,
      a plurality of receivers that measure the electromagnetic data after being produced at the plurality of transmitters and interacting with the object, and
      a boundary apparatus; and
   a processing center that, using the generated electromagnetic field data, repeatedly, in recursive manner, carries out steps of:
      forming an undisturbed electromagnetic interference image,
      forming a disturbed electromagnetic interference image based at least in part on the undisturbed electromagnetic interference image, wherein such step of forming a disturbed electromagnetic interference image is based at least in part on determination of an object factor that is a function of $$\frac{\left(\overline{E}_{ij}^{Sim} - \overline{E}_{ij}^{Exp}\right)}{\overline{M}_{ij}},$$

where $Ez_{ij}^{Sim \text{ or } Exp}$ is the experimentally simulated or measured value, respectively, of a z-component of the electromagnetic field measured by receiver j when transmitter i is the source of the electromagnetic field,
recognizing electromagnetic interference patterns in the repeatedly formed disturbed electromagnetic interference images, and
forming a superposition image by nullifying or diminishing the recognized electromagnetic interference patterns from the disturbed electromagnetic interference image.

2. The system of claim 1, wherein the object factor is determined as $$\frac{\left(\overline{E}_{ij}^{Sim} - \overline{E}_{ij}^{Exp}\right)}{\overline{M}_{ij}},$$

where $Ez_{ij}^{Sim\ or\ Exp}$ is the experimentally simulated or measured value, respectively, of a z-component of the electromagnetic field measured by receiver j when transmitter i is the source of the electromagnetic field, where $\overline{M}_{ij}$ is presented in a general form as $\alpha * f(E_{ij}^{Exp}) + \beta * (\Sigma_{ij} \overline{E}_{ij} * \Sigma_{ij} E_{ij}) + \gamma * \Omega$, where $\alpha, \beta$ and $\gamma$ are coefficients of real non-zero or zero values, where $\Omega$ is a regularization operator, and where $f(E_{ij}^{Exp})$ is a function of its argument.

3. The system of claim 1, wherein the object factor is determined as $$\frac{\left(Ez_{ij}^{Sim} - Ez_{ij}^{Exp}\right)}{\max\left\|\left(Ez_{ij}^{Exp}\right)\right\|},$$

where $Ez_{ij}^{Sim\ or\ Exp}$ is the experimentally simulated or measured value, respectively, of a z-component of the electromagnetic field measured by receiver j when transmitter i is the source of the electromagnetic field, and where $\max\|Ez_{ij}^{Exp}\|$ is the maximal norm of the experimentally measured z-component of the electromagnetic field.

4. The system of claim 1, wherein the object factor is determined as $$\frac{\left(Ez_{ij}^{Sim} - Ez_{ij}^{Exp}\right)}{\left\|\left(Ez_{ij}^{Exp}\right)\right\|^{\theta}},$$

where $Ez_{ij}^{Sim\ or\ Exp}$ is the experimentally simulated or measured value, respectively, of a z-component of the electromagnetic field measured by receiver j when transmitter i is the source of the electromagnetic field, and where $\|Ez_{ij}^{Exp}\|^{\theta}$ is the norm of the experimentally measured z-component of the electromagnetic field measured by receiver j when transmitter i is the source of the electromagnetic field in power of $\theta$.

5. The image reconstruction system of claim 1, wherein the step of forming a disturbed electromagnetic interference image based at least in part on the undisturbed electromagnetic interference image includes forming a disturbed electromagnetic interference image based at least in part on determination of an object factor that is a function of the differences between experimentally electromagnetic fields and electromagnetic fields calculated during the step of forming an undisturbed electromagnetic interference image.

6. The image reconstruction system of claim 1, wherein the processing center further carries out a step, carried out after each repeated step of forming a superposition image, of determining whether a convergence objective has been reached.

7. The image reconstruction system of claim 1, wherein the steps carried out by the processing center are used as part of a method of generating 4D differential (dynamic) fused images.

8. The image reconstruction system of claim 7, wherein generating 4D differential (dynamic) fused images includes combining at least one successively-formed images indicating relative physiological change with a baseline anatomical image for display as a single unified image.

9. The image reconstruction system of claim 8, wherein the method of generating 4D differential (dynamic) fused images is used as part of a method of monitoring viability and/or functional conditions of biological tissue utilizing 4D dynamic fused electromagnetic pattern recognition tomography.

10. The image reconstruction system of claim 1, wherein the steps of forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image are carried out sequentially.

11. The image reconstruction system of claim 1, further comprising a display unit that displays the superposition image.

12. An image reconstruction system using electromagnetic interference pattern recognition tomography, comprising:
an electromagnetic tomography system that generates electromagnetic field data corresponding to an object in an imaging domain, the electromagnetic tomography system including:
a plurality of electromagnetic transmitters,
a plurality of receivers that measure the electromagnetic data after being produced at the plurality of transmitters and interacting with the object, and
a boundary apparatus; and
a processing center that, using the generated electromagnetic field data, repeatedly, in recursive manner, carries out steps of:
forming an undisturbed electromagnetic interference image,
forming a disturbed electromagnetic interference image based at least in part on the undisturbed electromagnetic interference image, wherein such step includes forming a disturbed electromagnetic interference image based at least in part on determination of an object factor that is a function of the differences between experimentally electromagnetic fields and electromagnetic fields calculated during the step of forming an undisturbed electromagnetic interference image,
recognizing electromagnetic interference patterns in the repeatedly formed disturbed electromagnetic interference images, and forming a superposition image by nullifying or diminishing the recognized electromagnetic interference patterns from the disturbed electromagnetic interference image, and wherein the step of forming a disturbed electromagnetic interference image includes calculation of:

$$\sum_{i=1,N;j=1,M} \overline{E_i(f_k, x, y, z)} * E_j\overline{(f_k, x, y, z)} * \text{Object Factor}_{i,j}(f_k)$$

where $\overline{E_{i=1toN}(f_k,x,y,z)}$ and $\overline{E_{j=1toM}(f_k,x,y,z)}$ are 3D electromagnetic fields (x,y,z) distribution from electromagnetic sources of frequency $f_k$ located at the positions of physical sources (from 1 to N) in the electromagnetic tomography system and at the position of physical receivers (from 1 to M) correspondingly, taken as conjugate values, and wherein Object Factor$_{i,j}$ is the "ij"$^{th}$ component of the object factor, from transmitter i to receiver j.

13. The system of claim 12, wherein the step of forming a disturbed electromagnetic interference image includes calculation of $$\sum_{k=1,N} W_k \sum_{i=1,N;j=1M} \overline{E_i(f_k, x, y, z)} * E_j\overline{(f_k, x, y, z)} * \text{Object Factor}_{i,j}(f_k)$$

where $\overline{E_{i=1toN}(f_k,x,y,z)}$ and $\overline{E_{j=1toM}(f_k,x,y,z)}$ are 3D electromagnetic (x,y,z) distribution from electromagnetic sources of frequency $f_k$ located at the positions of physical sources (from 1 to N) in the electromagnetic tomography system and at the position of physical receivers (from 1 to M) correspondingly, taken as conjugate values, and wherein Object Factor$_{i,j}$ is the "ij"$^{th}$ component of the object factor, from transmitter i to receiver j.

14. The system of claim 12, wherein the step of recognizing electromagnetic interference patterns in the repeatedly formed disturbed electromagnetic interference images includes the calculation of sums $$\sum_{k=1,N} W_k \sum_{i=1,N;j=1M} \overline{E_i(f_k, x, y, z)} * E_j\overline{(f_k, x, y, z)} * \text{Object Factor}_{i,j}(f_k)$$

$\overline{E_{i=1toN}(f_k,x,y,z)}$ and $\overline{E_{j=1toM}(f_k,x,y,z)}$ are 3D electromagnetic (x,y,z) distribution from electromagnetic sources of frequency $f_k$ located at the positions of physical sources (from 1 to N) in the electromagnetic tomography system and at the position of the physical receivers (from 1 to M) correspondingly, taken as conjugate values, and wherein Object Factor$_{i,j}$ is the "ij"$^{th}$ component of the object factor, from transmitter i to receiver j.

15. The system of claim 12, wherein the step of recognizing electromagnetic interference patterns in the repeatedly formed disturbed electromagnetic interference images includes the calculation, for iteration i>1, $$\sum_{i=1,N;j=1,M}^{\text{at iteration } i} \overline{E_i(x, y, z)} * E_j\overline{(x, y, z)} * \text{Object Factor}_{i,j} -$$

$$\alpha * (\varepsilon^{i-1}(\bar{r}) - \varepsilon_{bkgd}) * \sum_{i=1,N;j=1,M}^{\text{at iteration } i-1} \overline{E_i(x, y, z)} * E_j\overline{(x, y, z)} * \text{Object Factor}_{i,j} -$$

$$(\varepsilon^{i-1}(\bar{r}) - \varepsilon_{bkgd})$$

where for simplicity the frequency terms are omitted, where $\overline{E_{i=}(x,y,z)}$ and $\overline{E_{j=}(x,y,z)}$ are 3D electromagnetic fields (x,y,z) distribution from electromagnetic sources located at the positions of physical sources (from 1 to N) in the electromagnetic tomography system and at the position of the physical receivers (from 1 to M) correspondingly, taken as conjugate values, and wherein Object Factor$_{i,j}$ is the "ij"$^{th}$ component of the object factor, from transmitter i to receiver j.

16. The system of claim 12, further comprising a step, carried out after each repeated step of forming a superposition image, of determining whether a convergence objective has been reached.

17. The system of claim 12, wherein the steps carried out by the processing center are used as part of a method of generating 4D differential (dynamic) fused images.

18. The system of claim 17, wherein generating 4D differential (dynamic) fused images includes combining at least one successively-formed images indicating relative physiological change with a baseline anatomical image for display as a single unified image.

19. The system of claim 18, wherein the method of generating 4D differential (dynamic) fused images is used as part of a method of monitoring viability and/or functional conditions of biological tissue utilizing 4D dynamic fused electromagnetic pattern recognition tomography.

20. The system of claim 12, wherein the steps of forming an undisturbed electromagnetic interference image, forming a disturbed electromagnetic interference image based at least in part on the undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image are carried out sequentially.

21. The system of claim 12, further comprising a step of displaying the superposition image via a display unit.

22. An image reconstruction system using electromagnetic interference pattern recognition tomography, comprising:
an electromagnetic tomography system that generates electromagnetic field data corresponding to an object in an imaging domain, the electromagnetic tomography system including:
a plurality of electromagnetic transmitters,
a plurality of receivers that measure the electromagnetic data after being produced at the plurality of transmitters and interacting with the object, and
a boundary apparatus; and
a processing center that, using the generated electromagnetic field data, repeatedly, in recursive manner, carries out steps of:
forming an undisturbed electromagnetic interference image,
forming a disturbed electromagnetic interference image based at least in part on the undisturbed electromagnetic interference image, wherein such step includes forming a disturbed electromagnetic interference image based at least in part on determination of an object factor that is a function of the differences between experimentally electromagnetic fields and electromagnetic fields calculated during the step of forming an undisturbed electromagnetic interference image, recognizing electromagnetic interference patterns in the repeatedly formed disturbed electromagnetic interference images, and forming a superposition image by nullifying or diminishing the recognized electromagnetic interference patterns from the disturbed electromagnetic interference image, and wherein the step of recognizing electromagnetic interference patterns in the repeatedly formed disturbed electromagnetic interference images includes the calculation of sums $$\sum_{k=1,N} W_k \sum_{i=1,N; j=1,M} \overline{E_i(f_k, x, y, z)} * E_j\overline{(f_k, x, y, z)} * \text{Object Factor}_{i,j}(f_k)$$

where $\overline{E_{i=1toN}(f_k,x,y,z)}$ and $\overline{E_{j=1toM}(f_k,x,y,z)}$ are 3D electromagnetic fields (x,y,z) distribution from electromagnetic sources of frequency $f_k$ located at the positions of physical sources (from 1 to N) in the electromagnetic tomography system and at the position of the physical receivers (from 1 to M) correspondingly, taken as conjugate values, and wherein Object Factor$_{i,j}$ is the "ij"$^{th}$ component of the object factor, from transmitter i to receiver j.

* * * * *